US009428729B2

(12) United States Patent
Antwiler et al.

(10) Patent No.: US 9,428,729 B2
(45) Date of Patent: *Aug. 30, 2016

(54) METHOD OF RESEEDING ADHERENT CELLS GROWN IN A HOLLOW FIBER BIOREACTOR SYSTEM

(71) Applicant: Terumo BCT, Inc., Lakewood, CO (US)

(72) Inventors: Glen Delbert Antwiler, Lakewood, CO (US); David A. Windmiller, Denver, CO (US); Monique Givens, Westminster, CO (US)

(73) Assignee: Terumo BCT, Inc., Lakewood, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/192,370

(22) Filed: Feb. 27, 2014

(65) Prior Publication Data

US 2014/0178995 A1  Jun. 26, 2014

Related U.S. Application Data

(63) Continuation of application No. 13/100,881, filed on May 4, 2011, now Pat. No. 8,691,565, which is a continuation-in-part of application No. 12/042,763, filed on Mar. 5, 2008, now abandoned.

(60) Provisional application No. 61/331,660, filed on May 5, 2010.

(51) Int. Cl.
*C12N 5/00* (2006.01)
*C12M 1/12* (2006.01)

(52) U.S. Cl.
CPC ............ *C12N 5/0068* (2013.01); *C12M 25/10* (2013.01); *C12M 25/12* (2013.01); *C12N 5/0025* (2013.01); *C12N 2500/14* (2013.01); *C12N 2500/16* (2013.01); *C12N 2500/34* (2013.01); *C12N 2509/00* (2013.01)

(58) Field of Classification Search
CPC ............ C12N 5/0025; C12N 2500/14; C12N 2500/16; C12N 2500/34
See application file for complete search history.

(56) References Cited

U.S. PATENT DOCUMENTS

| 4,391,912 | A | 7/1983 | Yoshida et al. |
| 4,647,539 | A | 3/1987 | Bach |
| 4,650,766 | A | 3/1987 | Harm et al. |
| 4,722,902 | A | 2/1988 | Harm et al. |
| 4,804,628 | A | 2/1989 | Cracauer et al. |
| 4,885,087 | A | 12/1989 | Kopf |
| 4,889,812 | A | 12/1989 | Guinn et al. |
| 4,894,342 | A | 1/1990 | Guinn et al. |
| 4,918,019 | A | 4/1990 | Guinn |
| 4,973,558 | A | 11/1990 | Wilson et al. |
| 5,079,168 | A | 1/1992 | Amiot |
| 5,100,799 | A | 3/1992 | Mundt |
| 5,126,238 | A | 6/1992 | Gebhard et al. |
| 5,162,225 | A | 11/1992 | Sager et al. |
| 5,202,254 | A | 4/1993 | Amiot et al. |
| 5,330,915 | A | 7/1994 | Wilson et al. |
| 5,399,493 | A | 3/1995 | Emerson et al. |
| 5,416,022 | A | 5/1995 | Amiot |
| 5,437,994 | A | 8/1995 | Emerson et al. |
| 5,459,069 | A | 10/1995 | Palsson et al. |
| 5,541,105 | A | 7/1996 | Melink et al. |
| 5,605,822 | A | 2/1997 | Emerson et al. |
| 5,622,857 | A | 4/1997 | Goffe |
| 5,631,006 | A | 5/1997 | Melink et al. |
| 5,635,386 | A | 6/1997 | Palsson et al. |
| 5,635,387 | A | 6/1997 | Fei et al. |
| 5,646,043 | A | 7/1997 | Emerson et al. |
| 5,656,421 | A | 8/1997 | Gebhard et al. |
| 5,670,147 | A | 9/1997 | Emerson et al. |
| 5,670,351 | A | 9/1997 | Emerson et al. |
| 5,688,687 | A | 11/1997 | Palsson et al. |
| 5,763,194 | A | 6/1998 | Slowiaczek et al. |
| 5,763,261 | A | 6/1998 | Gruenberg |
| 5,763,266 | A | 6/1998 | Palsson et al. |
| 5,882,918 | A | 3/1999 | Goffe |
| 5,888,807 | A | 3/1999 | Palsson et al. |
| 5,958,763 | A | 9/1999 | Goffe |

(Continued)

FOREIGN PATENT DOCUMENTS

| EP | 0220650 A2 | 5/1987 |
| WO | 86/02379 A1 | 4/1986 |
| WO | 88/01643 A1 | 3/1988 |
| WO | 90/02171 A1 | 3/1990 |
| WO | 91/07485 A1 | 5/1991 |
| WO | 95/04813 A1 | 2/1995 |
| WO | 95/11048 A2 | 4/1995 |
| WO | 95/21911 A1 | 8/1995 |
| WO | 00/75275 A2 | 12/2000 |
| WO | 03/105663 A2 | 12/2003 |
| WO | 2005/087915 A2 | 9/2005 |
| WO | 2007/136821 A1 | 11/2007 |
| WO | 2007/139742 A1 | 12/2007 |
| WO | 2007/139746 A1 | 12/2007 |
| WO | 2007/139747 A1 | 12/2007 |
| WO | 2007/139748 A2 | 12/2007 |
| WO | 2008/109668 A2 | 9/2008 |
| WO | 2008/109674 A2 | 9/2008 |
| WO | 2009/006422 A1 | 1/2009 |

OTHER PUBLICATIONS

Sigma Media Formulations. Datasheet [online]. Sigma-Aldrich, 2015 [retrieved Jul. 12, 2015] . Retrieved from the Internet: <URL:http://www.sigmaaldrich.com/life-science/cell-culture/learning-center/media-formulations.html>.*

(Continued)

*Primary Examiner* — Kara Johnson
(74) *Attorney, Agent, or Firm* — Elizabeth J. Reagan; John R. Merkling; René A. Pereyra

(57) ABSTRACT

This invention is directed to methods of directly reseeding harvested adherent cells grown in a hollow fiber bioreactor. Also disclosed is a novel harvest media for use in directly reseeding adherent cells into a hollow fiber bioreactor.

4 Claims, 3 Drawing Sheets

(56) References Cited

U.S. PATENT DOCUMENTS

| | | | |
|---|---|---|---|
| 5,981,211 | A | 11/1999 | Hu et al. |
| 5,985,653 | A | 11/1999 | Armstrong et al. |
| 5,994,129 | A | 11/1999 | Armstrong et al. |
| 5,998,184 | A | 12/1999 | Shi |
| 6,001,585 | A | 12/1999 | Gramer |
| 6,048,721 | A | 4/2000 | Armstrong et al. |
| 6,096,523 | A | 8/2000 | Parrott et al. |
| 6,096,532 | A | 8/2000 | Armstrong et al. |
| 6,168,944 | B1 | 1/2001 | Condon et al. |
| 6,228,635 | B1 | 5/2001 | Armstrong et al. |
| 6,238,908 | B1 | 5/2001 | Armstrong et al. |
| 6,326,198 | B1 | 12/2001 | Emerson et al. |
| 6,582,955 | B2 | 6/2003 | Martinez et al. |
| 6,616,912 | B2 | 9/2003 | Eddleman et al. |
| 6,667,034 | B2 | 12/2003 | Palsson et al. |
| 6,835,566 | B2 | 12/2004 | Smith et al. |
| 6,844,187 | B1 | 1/2005 | Weschler et al. |
| 6,943,008 | B1 | 9/2005 | Ma |
| 6,969,308 | B2 | 11/2005 | Doi et al. |
| 6,979,308 | B1 | 12/2005 | MacDonald et al. |
| 7,033,823 | B2 | 4/2006 | Chang |
| 7,041,493 | B2 | 5/2006 | Rao |
| 7,172,696 | B1 | 2/2007 | Martinez et al. |
| 7,270,996 | B2 | 9/2007 | Cannon et al. |
| 7,682,822 | B2 | 3/2010 | Noll et al. |
| 8,685,728 | B2 | 4/2014 | Shi et al. |
| 8,691,565 | B2 | 4/2014 | Antwiler et al. |
| 2007/0122904 | A1 | 5/2007 | Nordon |
| 2008/0194010 | A1 | 8/2008 | Liu |
| 2008/0220522 | A1 | 9/2008 | Antwiler |

OTHER PUBLICATIONS

Office Action, Chinese Patent Application No. 201180021315.9, Jun. 5, 2014 (English language translation included).

Office Action, Chinese Patent Application No. 201180021315.9, Dec. 11, 2014 (English language translation included).

Ala-Uotila, Sari et al., "Use of a hollow fiber bioreactor for large-scale production of a2-adrenoceptors in mammalian cells", Journal of Biotechnology, 1994, pp. 179-184, vol. 37.

Chang, Ho Nam, "Membrane Bioreactors: Engineering Aspects", Biotech. Adv., 1987, pp. 129-145, vol. 5.

Chang, Ho Nam and Furusaki, Shiataro, "Membrane Bioreactors: Present and Prospects", Advances in Biochemical Engineering, 1991, pp. 27-64, vol. 44.

Edgington, Stephen M., "New Horizons for Stem-Cell Bioreactors", Biotechnology, Oct. 1992, pp. 1099-1106, vol. 10.

Freshney, R. Ian, "Chapter 8: Defined Media and Supplements", Culture of Animal Cells: A Manual of Basic Technique and Specialized Applications, Sixth Edition, 2010, pp. 99-114, John Wiley & Sons, Inc.

Freshney, R. Ian, "Chapter 11: Primary Culture", Culture of Animal Cells: A Manual of Basic Technique and Specialized Applications, Sixth Edition, 2010, pp. 163-186, John Wiley & Sons, Inc.

Freshney, R. Ian, "Chapter 12: Subculture and Cell Lines", Culture of Animal Cells: A Manual of Basic Technique and Specialized Applications, Sixth Edition, 2010, pp. 187-206, John Wiley & Sons, Inc.

Gastens, Martin H. et al., "Good Manufacturing Practice-Compliant Expansion of Marrow-Derived Stem and Progenitor Cells for Cell Therapy", Cell Transplantation, 2007, pp. 685-696, vol. 16.

Gramer, Michael J. and Poeschl, Douglas M., "Screening Tool for Hollow-Fiber Bioreactor Process Development", Biotechnol. Prog., 1998, pp. 203-209, vol. 14, No. 2.

Hirschel, M.D. and Gruenberg, M.L., "An Automated Hollow Fiber System for the Large Scale Manufacture of Mammalian Cell Secreted Product", Large Scale Cell Culture Technology, 1987, pp. 111-144, Hansen Publishers.

International Search Report, PCT/US2008/055904, Jan. 16, 2009.

International Search Report and Written Opinion, PCT/US2011/035210, Oct. 24, 2011.

Invitation to Pay Additional Fees and, Where Applicable, Protest Fee and Partial International Search Report, PCT/US2011/035210, Aug. 2, 2011.

Nielsen, Lars Keld, "Bioreactors for Hematopoietic Cell Culture", Annu. Rev. Biomed. Eng. 1999, pp. 129-152, vol. 01.

Office Action, Chinese Patent Application No. 201180021315.9, Oct. 8, 2013 (English language translation included).

Portner, Ralf and Giese, Christoph, "An Overview on Bioreactor Design, Prototyping and Process Control for Reproducible Three-Dimensional Tissue Culture", Drug Testing In Vitro: Breakthroughs and Trends in Cell Culture Technology, 2007, pp. 53-78.

Written Opinion of the International Search Authority, PCT/US2011/035210, Oct. 24, 2011.

Zhao, Feng and Ma, Teng, "Perfusion Bioreactor System for Human Mesenchymal Stem Cell Tissue Engineering: Dynamic Cell Seeding and Construct Development", Biotechnology and Bioengineering, Aug. 20, 2005, pp. 482-493, vol. 91, No. 4.

Communication pursuant to Article 94(3) EPC, European Patent Application No. 11720927.0, Oct. 3, 2014.

Office Action, Japanese Patent Application No. 2013-509222, Jun. 16, 2015 (English language translation included).

Office Action, Japanese Patent Application No. 2013-509222, Apr. 21, 2016 (English language translation included).

* cited by examiner

METHOD OF RESEEDING ADHERENT CELLS GROWN IN A HOLLOW FIBER BIOREACTOR SYSTEM

CROSS-REFERENCE TO RELATED APPLICATIONS

This patent application is a continuation of, and claims priority to, U.S. patent application Ser. No. 13/100,881, entitled, "METHOD OF RESEEDING ADHERENT CELLS GROWN IN A HOLLOW FIBER BIOREACTOR SYSTEM," filed May 4, 2011 and issued as U.S. Pat. No. 8,691,565 on Apr. 8, 2014. U.S. patent application Ser. No. 13/100,881 claims priority to U.S. Provisional Patent Application Ser. No. 61/331,660, filed May 5, 2010, and is a continuation-in-part of U.S. patent application Ser. No. 12/042,763, filed Mar. 5, 2008. The disclosures of the above-identified applications are hereby incorporated by reference in their entireties as if set forth herein in full for all that they teach and for all purposes.

BACKGROUND OF THE INVENTION

The use of stem cells in a variety of treatments and therapies is receiving growing attention. Stem cells can be used to repair or replace damaged or defective tissues and have broad clinical applications for treating a wide range of diseases.

Cell expansion systems can be used to grow stem cells, as well as other types of cells, both adherent and non-adherent. Adherent cells require a surface to attach to before the cells will grow and divide. Non-adherent cells grow and divide while floating in suspension.

Cell expansion systems provide nutrients to the growing cells and remove metabolites, as well as furnishing a physiochemical environment conducive to cell growth. Cell expansion systems are known in the art.

As a component of a cell expansion system, a bioreactor, or cell growth chamber, plays an important role in providing an optimized environment for the expanding cells. There are many types of bioreactors known in the art. Bioreactor devices include culture flasks, roller bottles, shaker flasks, stirred-tank reactors, air-lift reactors and hollow fiber bioreactors.

Once expanded cells in a bioreactor reach either confluence or the desired number of cells, they need to be harvested, and if further growth is desired, the cells need to be reseeded into the same or different bioreactor.

Regardless of which type of bioreactor device is used, to harvest adherent cells, the cells must first be removed from the surface they are growing on. In order to remove the adherent cells from the growth surface, the cells are initially washed to remove ions which inhibit trypsin (magnesium, calcium). Typsin is then added to the washed cells to loosen them from the surface. Once the cells are loosened, they are removed from the membrane surface and processed to remove the trypsin either by washing the removed cells or spinning them down into a pellet, removing the surrounding fluid and suspending them in new growth media.

This procedure is easily done in open systems, such as culture flasks where the procedure takes place in a laminar flow hood, with the cells growing on flat plates. However, in closed systems using a hollow fiber bioreactor, the system is closed to the atmosphere. There is no easy way to add or remove fluids from the system, and ions contained in the growth media necessary for cell growth are lost from the cellular growth space due to ultrafiltration across the hollow fibers. The cells are therefore living in an environment surrounded by diluted media, (from the addition of fluid into the system from the initial washing of the cells) trypsin (from the trypsin used to loosen the cells from the membrane) and no ions in the media (calcium and magnesium for example) as a result of ultrafiltration.

These factors may contribute to the lack of cell growth of harvested adherent cells which are directly reseeded into a hollow fiber bioreactor.

Therefore, new reseeding protocols need to be developed for use in cell expansion systems using a hollow fiber bioreactor.

BRIEF SUMMARY OF THE INVENTION

This invention is directed to methods for directly reseeding harvested adherent cells grown in a hollow fiber bioreactor having an intracapillary space and an extracapillary space wherein the cell growth space is one of the intracapillary space or the extracapillary space. The method includes the steps of removing growth media from the cell growth space; washing the cells to remove residual growth media from the cell growth space; loosening the cells from the hollow fibers of the hollow fiber bioreactor by adding trypsin to the cell growth space; removing the cells and any trypsin from the cell growth space; inactivating the trypsin from the removed cells; and directly reseeding the removed cells and trypsin into the cell growth space of a hollow fiber bioreactor.

This invention also claims a method of making harvest media for use in directly reseeding adherent cells into a hollow fiber bioreactor by calculating the amount of ions and protein needed in the media using $C_h v_h + 0 v_{circuit} = c_f v_h + c_c v_c$ and adding the calculated amounts of ions and protein to the media.

DETAILED DESCRIPTION OF THE INVENTION

The present disclosure is generally directed to sterile methods for harvesting and/or reseeding adherent cells, in particular mesenchymal stem cells, from a hollow fiber cell growth chamber/bioreactor of a closed cell expansion system. A closed system means that the system is not directly exposed to the atmosphere.

Harvesting the expanded cells from the cell expansion system includes removing all the expanded cells from the bioreactor. Reseeding the harvested cells includes reloading all of the removed cells into the same or different bioreactor for further expansion; or reloading a portion of the harvested cells into the same or different bioreactor while retaining the remaining portion of the removed cells for later use.

Figure 1:
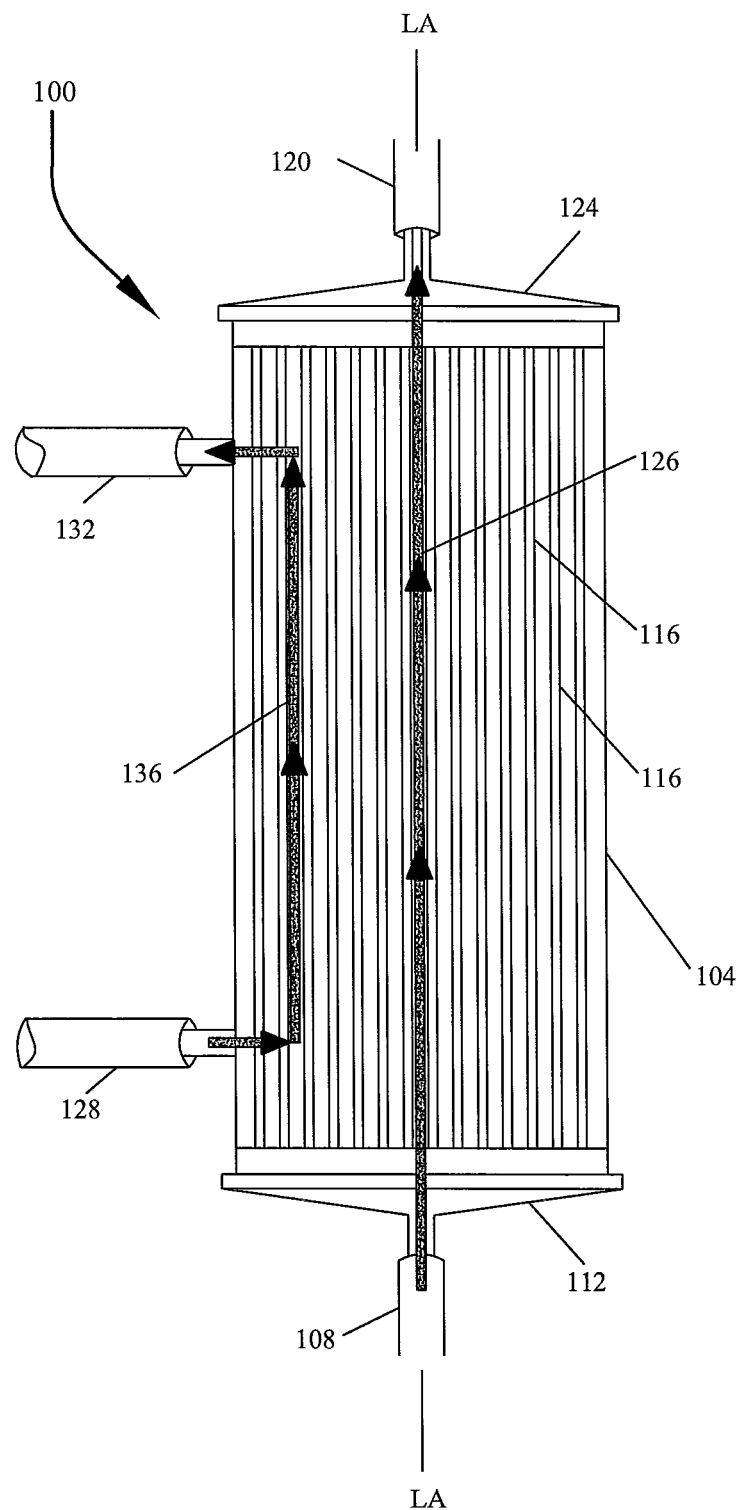
FIG. 1 is a schematic illustration of the hollow fiber bioreactor useful in the present invention.

With reference now to FIG. 1, an example of a hollow fiber cell growth chamber 100 which may be used with the present invention is shown in front side elevation view. Cell growth chamber 100 has a longitudinal axis LA-LA and includes cell growth chamber housing 104. In at least one embodiment, cell growth chamber housing 104 includes four openings or ports: IC inlet port 108, IC outlet port 120, EC inlet port 128, and EC outlet port 132. It should be noted that in the figures, like elements are represented by like numerals. The direction of fluid flow through the bioreactor 100 (FIG. 1) and cell expansion system 200 (FIG. 2) is indicated by arrows.

A plurality of hollow fibers 116 are disposed within cell growth chamber housing 104. The material used to make the hollow fibers 116 may be any biocompatible polymeric material which is capable of being made into hollow fibers. The terms "hollow fiber," "hollow fiber capillary," and "capillary" are used interchangeably. A plurality of hollow fibers are called a membrane.

The ends of the hollow fibers 116 can be potted to the ends of the cell growth chamber housing 104 by a connective material (also referred to herein as "potting" or "potting material"). The potting can be any suitable material for binding the hollow fibers 116, provided that the flow of culture media (and cells if desired) into the hollow fibers is not obstructed. Exemplary potting materials include, but are not limited to, polyurethane or other suitable binding or adhesive components. End caps 112 and 124 respectively, are disposed at each end of the mass transfer device.

Cell growth media in a first circulation path 202 (see FIG. 2) enters cell growth chamber 100 through IC inlet port 108 at a first longitudinal end 112 of the cell growth chamber 100, passes into and through the intracapillary side (referred to in various embodiments as the intracapillary ("IC") side or "IC space") of the hollow fibers 116, and out of cell growth chamber 100 through IC outlet port 120 located at a second longitudinal end 124 of the cell growth chamber 100. The fluid path between the IC inlet port 108 and the IC outlet port 120 defines the IC portion 126 of the cell growth chamber 100.

Fluid in a second circulation path 204 (see FIG. 2) flows into the cell growth chamber 100 through EC inlet port 128, comes in contact with the extracapillary side or outside (referred to as the "EC side" or "EC space") of the hollow fibers 116, and exits cell growth chamber 100 via EC outlet port 132. The fluid path between the EC inlet port 128 and the EC outlet port 132 comprises the EC portion 136 of the cell growth chamber 100. Fluid entering cell growth chamber via the EC inlet port 128 is in contact with the outside of the hollow fibers 116.

Small molecules (e.g., ions, water, oxygen, lactate, etc.) can diffuse through the hollow fibers from the IC space to the EC space, or from the EC space to the IC space. Large molecular weight molecules such as growth factors are typically too large to pass through the hollow fiber membrane, and remain in the IC space of the hollow fibers. The media may be replaced as needed. Media may also be circulated through a gas transfer module/oxygenator 232 to exchange gasses as needed.

Cells are typically contained within the IC space of the hollow fibers in the first circulation path 202, but may also be contained within the EC space in the second circulation path 204, without departing from the spirit and scope of the invention. Cells are grown in the cell growth space regardless of whether the cells are grown in the IC space or EC space.

The material used to make the hollow fiber membrane may be any biocompatible polymeric material which is capable of being made into hollow fibers.

Figure 2:
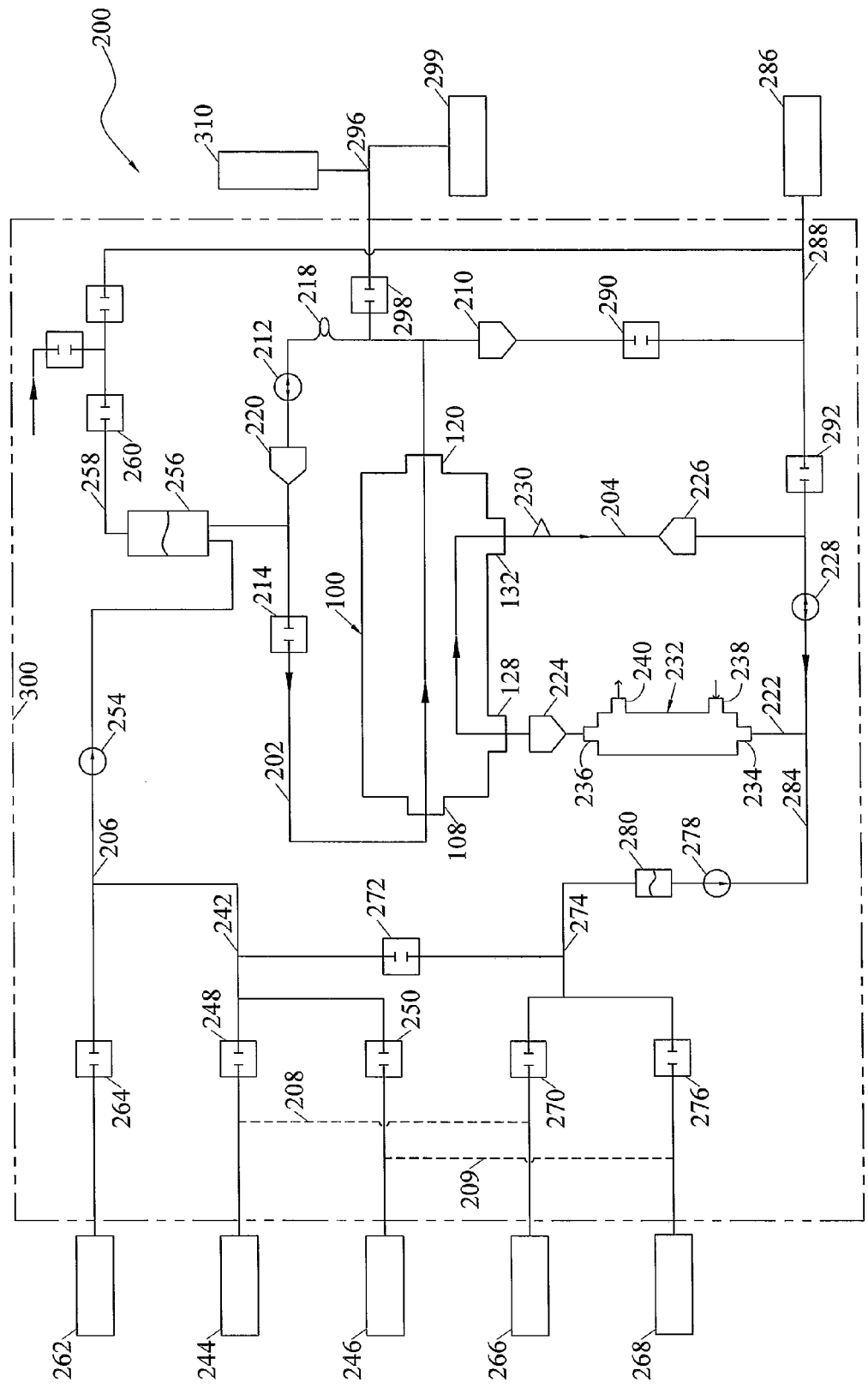
FIG. 2 shows a schematic illustration of a cell expansion system which may be used with the present invention.

FIG. 2 shows a schematic of one embodiment of a cell expansion system which may be used with the present invention.

First fluid flow path 206 is fluidly associated with cell growth chamber 100 to form first fluid circulation path 202. Media is in contact with the inside of the hollow fibers in the cell growth chamber 100. Fluid flows into cell growth chamber 100 through IC inlet port 108, through hollow fibers in cell growth chamber 100, and exits via IC outlet port 120. Pressure gauge 210 measures the pressure of media leaving cell growth chamber 100. Media flows through IC circulation pump 212 which can be used to control the rate of media flow in the IC loop 202. Media then flows through valve 214. As those skilled in the art will appreciate, additional valves and/or other devices can be placed at various locations to isolate and/or measure characteristics of the media along portions of the fluid paths. Accordingly, it is to be understood that the schematic shown represents one of many possible configuration for various elements of the cell expansion system and modifications to the schematic shown are within the scope of the one or more present inventions.

With regard to the IC loop, samples of media can be obtained from sample coil 218 during operation. Pressure/temperature gauge 220 disposed in first fluid circulation path 202 allows detection of media pressure and temperature during operation. Media then returns to IC inlet port 108 to complete fluid circulation path 202. Cells grown/expanded in cell growth chamber 100 can be flushed out of cell growth chamber 100 into harvest bag 299 or can be redistributed within the hollow fibers for further growth. This will be described in more detail below.

Second fluid circulation path 204 includes second fluid flow path 284 that is fluidly associated with cell growth chamber 100 in a loop. Fluid in second fluid circulation path 204 enters cell growth chamber 100 via EC inlet port 128, and leaves cell growth chamber 100 via EC outlet port 132.

Pressure/temperature gauge 224 disposed in the second fluid circulation path 204 allows the pressure and temperature of media to be measured before the media enters the EC space of the cell growth chamber 100. Pressure gauge 226 allows the pressure of media in the second fluid circulation path 204 to be measured after it leaves the cell growth chamber 100. With regard to the EC loop, samples of media can be obtained from sample port 230 or a sample coil (not shown) during operation.

After leaving EC outlet port 132 of cell growth chamber 100, fluid in second fluid circulation path 204 passes through EC circulation pump 228 to gas transfer module 232. Second fluid flow path 222 is fluidly associated with gas transfer module 232 via gas transfer module inlet port 234 and outlet port 236. In operation, fluid media flows into gas transfer module 232 via inlet port 234, and exits gas transfer module 232 via outlet port 236. Gas transfer module 232 adds gas to and removes excess gas (bubbles) from media in the cell expansion system. In various embodiments, media in second fluid circulation path 204 is in equilibrium with gas entering gas transfer module 232. The gas transfer module 232 can be any appropriately sized module known in the art. Air or gas flows into gas transfer module 232 via filter 238 and out of gas transfer module 232 through filter 240. Filters 238 and 240 reduce or prevent contamination of gas transfer module 232 and associated media. Air or gas purged from the system 200 during portions of the priming sequence can vent to the atmosphere via the gas transfer module 232.

In the configuration shown, fluid media in first fluid circulation path 202 and second fluid circulation path 204 flows through cell growth chamber 100 in the same direction (co-current configuration). The cell expansion system 200 can also be configured to flow in different directions (counter-current configuration).

Cells (from bag 262) and IC fluid media (from bag 246) can be introduced into first fluid circulation path 202 via first fluid flow path 206. Fluid containers 244 (e.g., Reagent) and 246 (e.g., IC Media) may be fluidly associated with either first fluid inlet path 242 via valves 248 and 250 respectively, or second fluid inlet path 274 via valves 270 and 276. For purposes of priming the various inlet paths, first and second sterile sealable input priming paths 208 and 209 are provided. Air removal chamber 256 is fluidly associated with first circulation path 202. The air removal chamber 256 may include one or more ultrasonic sensors to detect air or the lack of fluid at certain measuring positions within the air removal chamber 256. For example, ultrasonic sensors may be used near the bottom and/or near the top of the air removal chamber 256 to detect air or fluid at these locations. Air or gas purged from the cell expansion system 200 during portions of the priming sequence can vent to the atmosphere out air valve 260 via line 258 that is fluidly associated with air removal chamber 256.

Fluid container 262 (e.g., Cell Inlet Bag (or Saline Priming Fluid)) is fluidly associated with the first fluid circulation path 202 via valve 264. EC media (from bag 268) or wash solution (from bag 266) may be added to either the first or second fluid flow path.

Fluid container 266 may be fluidly associated with valve 270 that is fluidly associated with first fluid circulation path 202 via distribution valve 272 and first fluid inlet path 242. Alternatively, fluid container 266 can be fluidly associated with second fluid circulation path 204 via second fluid inlet path 274 and second fluid flow path 284 by opening valve 270 and closing distribution valve 272. Likewise, fluid container 268 is fluidly associated with valve 276 that may be fluidly associated with first fluid circulation path 202 via first fluid inlet path 242. Alternatively, fluid container 268 may be fluidly associated with second fluid inlet path 274 by opening valve 276 and closing valve distribution 272.

In the IC loop, fluid is initially advanced by the IC inlet pump 254. In the EC loop, fluid is initially advanced by the EC inlet pump 278. An air detector 280, such as an ultrasonic sensor, may also be associated with the second fluid flow path 284.

In at least one embodiment, first and second fluid circulation paths 202 and 204 are connected to waste line 288. When valve 290 is opened, IC media can flow through waste line 288 and to waste bag 286. Likewise, when valve 292 is opened, EC media can flow through waste line 288 to waste bag 286.

Cells can be harvested via cell harvest path 296. Here, cells from cell growth chamber 100 can be harvested by pumping the IC media containing the cells through cell harvest path 296 and valve 298 to cell harvest bag 299.

Various components of the cell expansion system 200 can be contained or housed within an incubator 300, wherein the incubator maintains cells and media at a desirable temperature.

As will be recognized by those of skill in the art, any number of fluid containers (e.g., media bags) can be fluidly associated with the cell expansion system in any combination.

The cell growth media used in the system (both on the IC and EC sides) is typically complete media, which means that the media contains at least some percentage of a protein. Examples of protein commonly used in cell growth media include human platelet lysate, human plasma, fetal bovine serum (FBS) and/or fetal calf serum (FCS). The terms cell growth media and complete media are used interchangeably. Base media is cell growth media without a protein source. An example of a base media useful in this invention is alpha-MEM, however, any commonly used media without protein may be used in this invention.

If it is desired to reseed/reload the bioreactor for further cell expansion, or to harvest the expanded cells for ultimate clinical use, a cell harvesting protocol to remove the cells from the membrane must be initiated. The bioreactor can be completely or partially reseeded, depending on the final number of cells desired. The purpose of reseeding the bioreactor is to release the cells from the membrane surface and to reload them into the same or different bioreactor for continuing expansion.

However, if the cells flushed out of the bioreactor after undergoing a harvest procedure are directly reseeded into the same or different bioreactor they do not grow. Directly reseeded means that the cells removed from the bioreactor are not subjected to any additional procedures before being reseeded. This is shown in Table 1 below.

In this experiment, the media in the IC loop 202 and EC loop 204 was exchanged with PBS to remove complete media as well as magnesium and calcium ions from both the IC and EC loops of the system. A trypsin solution was introduced from bag 244 (or 246, 266 or 268) into the first fluid circulation path 202. After a dwell period to allow the trypsin to detach the cells from the IC membrane, complete media was re-introduced into the first fluid circulation path 202 from bag 246 (or 244,266 or 268) to inactivate the trypsin and to push the cells out of the IC side of the bioreactor through tubing line 296 and into the cell harvest bag 299. The cells were taken directly from the cell harvest bag 299 and either loaded directly into a new bioreactor, or spun down and washed in 100 mL base media before being loaded into a new bioreactor.

As seen in Table 1, growth was far better in a bioreactor which was loaded with a cell product that was subjected to a washing step to replace the fluid before loading it into a new bioreactor.

TABLE 1

| Direct load - no washing before load | | Initial wash before load | |
| --- | --- | --- | --- |
| No. cells initially loaded | No. of cells after harvesting | No. cells initially loaded | No. of cells after harvesting |
| $3.63 \times 10^7$ | $23.6 \times 10^7$ | $3.86 \times 10^7$ | $42.4 \times 10^7$ |

As seen from the table, washing harvested cells before reseeding them into a hollow fiber bioreactor produces greater cell growth than directly loading cells into a hollow fiber bioreactor. However, a washing step is a place where contamination of the expanded cells can occur, and is an additional step in the cell expansion process. A procedure that would allow harvested cells to be directly reseeded without any additional washing steps would be advantageous.

Therefore, as an alternative to washing the cells, a protein source such as FBS (as one example, not meant to be limiting) could be added to harvest bag 299 prior to connecting to the cell expansion system 200 (so that the concentration of protein in the harvest bag is 100%). Protein could also be added to base media (to make complete media) in any concentration between 1-100% before the harvested cells flow into the bag. The additional concentration of protein would be diluted in the harvest bag by the harvested cells (plus trypsin plus the media used to push the cells out of the bioreactor) to help create a more normal environment for the cells, which could be directly reseeded.

In another embodiment, before a harvest procedure is started, either complete media or protein alone from any of bags 244, 246, 266 or 268 could be pumped via pumps 212 or 254 into harvest bag 299. Complete media or protein would be pumped into harvest bag 299 at a faster rate than the rate the media with the cells is traveling through the IC side of the bioreactor, so that by the time the harvested cells reached the harvest bag, the bag would already be full of complete media or protein.

Protein alone or complete media could also be added directly into tubing line 296 which carries the cells out of the bioreactor and into the harvest bag 299. In this embodiment, protein or complete media could be pumped from bag 310 directly into line 296 at any point along the line. The cells would be washed out of bioreactor 100 from port 120 and into line 296. The cells would be mixed with the protein source or complete media in tubing 296 and would immediately be in an environment conducive to cell growth. The cells could be directly reseeded.

In the described embodiments, the trypsin contained in the media suspending the harvested cells would be immediately neutralized upon exposure to the protein source, and the cells could be directly reseeded into a new or the same bioreactor, without an additional washing step. These procedures also make the cells more viable immediately after a harvest procedure, since before this invention, as previously practiced, the cells were living for some period of time in a protein free environment, as all protein was removed from the cellular environment during the harvest procedure. Lack of protein is not conducive to cell growth.

To compensate for the lack of ions in the cellular environment which occurs as a result of harvesting the cells in a closed hollow fiber system, a novel harvest media was developed. An advantage of using this harvest media to directly reseed adherent cells such as mesenchymal stem cells harvested from a hollow fiber bioreactor is that the harvest media has enough metabolites present to compensate for the lack of ions in the cellular environment and enable the cells to begin growing immediately after reseeding.

Table 2 below compares the concentrations of ions in base media to that of the novel harvest media. In this example, the base media used is alpha-MEM. As seen in the table, the constituents of base media and harvest media are the same, however, the harvest media has a higher concentration of calcium, magnesium and glucose to compensate for the loss of those metabolites through the hollow fibers during a harvest procedure.

TABLE 2

| Metabolite | Base Media | Harvest Media |
| --- | --- | --- |
| Calcium chloride | 1.4 mM | 3.9 mM |
| Anhydrous D-glucose | 5.3 mM | 9.91 mM |
| Magnesium Sulfate | 0.81 mM | 2.24 mM |

The harvest media in the above example is prepared as follows:
1. Add 7.41 g anhydrous D-glucose (Sigma #G5767) and 3.37 g dihydrate calcium chloride (Sigma#C3306) to a final volume of 50mL alpha-MEM (Lonza#12-169-F). Mix until dissolved. In a separate tube, add 3.25 g heptahydrate magnesium sulfate (Sigma#M1880) to a final volume of 50 mL alpha-MEM. Mix until dissolved.
2. Add the above 50mL glucose/calcium solution to an additional 3060 mL alpha-MEM, 50 mL 100× glutamax (Gibco#35050) and 800 mL FBS (Gibco#12662-029). Add 50 mL magnesium solution after adding glucose/calcium solution. Store @ 4° C.

Table 3 shows that cells collected and directly reseeded in harvest media are able to begin growing immediately after attachment to the membrane. The data shown is for a full reseeding procedure.

TABLE 3

| Number of live cells reseeded | % attachment to membrane | Time period for attachment and growth to confluence after reseeding | Number of cells harvested |
| --- | --- | --- | --- |
| $28.2 \times 10^6$ | 97.7% | 5.9 days | $73.2 \times 10^6$ |

Figure 3:
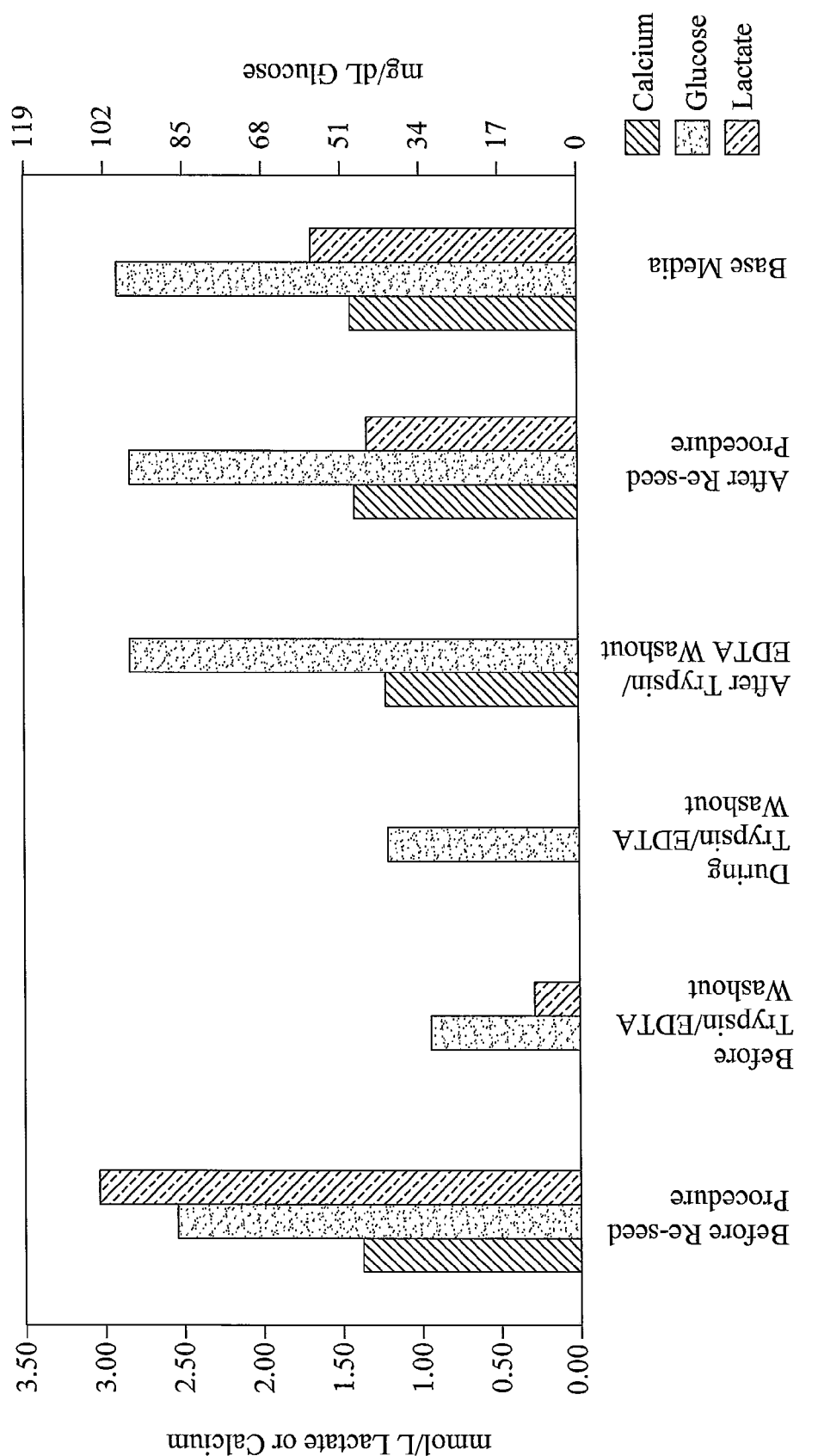
FIG. 3 is a graph showing metabolite concentrations before, during and after a full reseeding procedure according to the present invention.

FIG. 3 is a graph showing metabolite concentrations in the IC media before, during, and after a full reseeding procedure. Before the reseeding procedure, the concentration of calcium in the growth media was near baseline, where baseline refers to the amount of calcium found in base alpha-MEM media. Concentrations of glucose and lactate were lower and higher than baseline, respectively, which reflected the metabolic activity of growing mesenchymal stem cells. Before the trypsin/EDTA (ethylenediaminetetraacetic acid) washout step of the procedure, calcium was below the limit of detection. Glucose and lactate levels had also decreased significantly, due to the media exchange with PBS. Glucose levels were higher than lactate because trypsin/EDTA contains glucose. As base media was flushed into the system during the trypsin/EDTA washout, glucose levels began to rise and lactate levels dropped to below the limit of detection, since base media contains glucose, but not lactate. After the washout, calcium and glucose levels returned to baseline. After the re-seeding procedure was completed, lactate levels also returned to baseline.

In this example, the base media used is alpha-MEM. However, one skilled in the art would know that additional amounts of calcium, magnesium and glucose can be added to any base media desired.

If other media besides alpha-MEM is used, the following equation can be used to calculate the additional amount of ions and protein needed to make any base media into harvest media for use in a hollow fiber system.

$$C_h v_h + 0 v_{circuit} = c_f v_h + c_c v_c$$

where $c_h$=initial concentration of harvest media
$v_h$=volume of harvest media that is removed from system
0=protein (because none in system)
$Ca^{++}$ and $Mg^{++}$ are also 0 (because none in system)
$c_f$=concentration of harvest media desired (final)
$v_h$=volume of harvest media that is added to system
$c_c$=final mixed concentration ($c_{IC}v_{IC}+c_{EC}v_{EC}$)
$v_c$=final volume of IC loop Though the description of the invention has included descriptions of one or more embodiments and certain variations and modifications, other variations and modifications are within the scope of the invention as may be within the skill and knowledge of those in the art. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publically dedicate any patentable subject matter.

The invention claimed is:

1. A media for harvesting cells grown in a hollow fiber bioreactor, the media comprising:
   base media;
   protein;
   3.9 mM calcium chloride;
   9.91 mM anhydrous D-glucose; and
   2.24 mM magnesium sulfate.

2. The media of claim 1, wherein the base media comprises alpha-MEM.

3. The media of claim 1, wherein the protein comprises one or more from the group consisting of: human platelet lysate, human plasma, fetal bovine serum, and fetal calf serum.

4. The media of claim 1, wherein the media is used to compensate for a loss of metabolites through hollow fibers of the hollow fiber bioreactor during a harvest procedure.

* * * * *